United States Patent [19]

Wardell

[11] 4,421,762

[45] Dec. 20, 1983

[54] METHOD OF TREATMENT OF AN ALLERGY TO AN INGESTED ALLERGEN

[75] Inventor: George Wardell, Loughborough, England

[73] Assignee: Fisons Limited, London, England

[21] Appl. No.: 300,281

[22] Filed: Sep. 8, 1981

Related U.S. Application Data

[63] Continuation-in-part of Ser. No. 941,632, Sep. 12, 1978, abandoned, which is a continuation-in-part of Ser. No. 755,606, Dec. 29, 1976, Pat. No. 4,152,448, which is a continuation of Ser. No. 471,139, May 17, 1974, abandoned, which is a continuation-in-part of Ser. No. 329,417, Feb. 5, 1973, abandoned.

[30] Foreign Application Priority Data

Feb. 15, 1972 [GB] United Kingdom ................. 6911/72
Feb. 2, 1974 [GB] United Kingdom ................. 4912/74

[51] Int. Cl.$^3$ ............................................ A61K 31/35
[52] U.S. Cl. .................................................. 424/283
[58] Field of Search ........................................ 424/283

[56] References Cited

U.S. PATENT DOCUMENTS 3,686,412  8/1972  Fitzmaurice et al. ................ 424/283

OTHER PUBLICATIONS

The Lancet, Jul. 20, 1968, 134–137.
The Journal of Pediatrics, Oct. 1969, vol. 75, No. 4, 623–631.
The Lancet, Oct. 31, 1970, 893–895.
The Lancet, Apr. 28, 2973, 913–915.

Primary Examiner—Frederick E. Waddell
Attorney, Agent, or Firm—Wenderoth, Lind & Ponack

[57] ABSTRACT

There is described a method of treatment of allergy to ingested allergens, which comprises per os administration of a daily dosage of from 20 to 4,000 mg of 1,3-bis(2-carboxychromon-5-yloxy)-2-hydroxypropane or a therapeutically acceptable salt thereof to a patient having such an allergy.

8 Claims, No Drawings

METHOD OF TREATMENT OF AN ALLERGY TO AN INGESTED ALLERGEN

This application is a continuation-in-part of application Ser. No. 941,632, filed Sept. 12, 1978 (now abandoned) which in turn is a continuation-in-part of Ser. No. 755,606, filed Dec. 29, 1976 (now U.S. Pat. No. 4,152,448), which application is a continuation of application Ser. No. 471,139, filed May 17, 1974 (now abandoned), the latter application being a continuation-in-part of application Ser. No. 329,417, filed Feb. 5, 1973 (now abandoned).

This invention relates to a new therapeutic method.

In U.S. Pat. No. 3,686,412 there are described a large number of bis-chromonyl compounds and their use in the treatment of asthma. These compounds are described as being administered orally, parenterally or more preferably by way of inhalation. These compounds are in general large and highly polar molecules and as such would not be expected to be absorbed through the gut to a sufficient extent to provide therapeutic levels of the compounds in the sub-epithelial tissues.

Adverse reactions to foods are common, particularly in children, but the underlying mechanisms are to a great extent unknown. In several cases, despite strict diets, eliminating all suspected offending foods, the child is never entirely symptom free and in patients allergic to several basic foods nutritional problems may occur.

Surprisingly we have now found that 1,3-bis(2-carboxychromon-5-yloxy)propan-2-ol and its therapeutically acceptable salts are useful in the treatment of allergy to ingested allergens, most importantly allergy to certain foods. Even more surprisingly, particularly as the compounds are at most only 1% absorbed from the gastro-intestinal tract, it has been found that they can have a remarkable effect on food allergic symptoms which occur in organs remote from the gastro-intestinal tract.

For many years food allergy has been a considerable problem, and, before the present invention, there was no known and effective drug treatment, let alone a prophylactic treatment, for this distressing problem. Indeed prior to the present invention the only practical method of treating food allergy was an elimination diet, which when common foodstuffs, e.g. egg or gluten are implicated, is extremely difficult to keep to.

The disodium salt of 1,3-bis(2-carboxychromon-5-yloxy)-2-hydroxypropane is known to be active as an antiallergic when administered to the lung, but is also known (Assem and Mongar Int. Arch. Allergy, Vol 38, (1970) pages 68–77 at page 75) to be tissue specific and is therefore, according to the prior art, of doubtful utility in allergies which involve other tissues. In Clin. exp. Immunol (1975) 21,419–429, particularly at page 424, it is stated that the disodium salt of 1,3-bis(2-carboxychromon-5-yloxy)-2-hydroxypropane when administered orally is not effective to inhibit allergic reactions in rats.

Furthermore, the mechanism of allergy in the lung, and even more so in the gastro-intestinal tract, is obscure and there are no grounds for prediction from one organ to the other.

According to the invention there is provided a method of treatment of allergy to ingested allergens, which comprises per os administration of a daily dosage of from 20 to 4,000 mg of 1,3-bis(2-carboxychromon-5-yloxy)-2-hydroxypropane or a therapeutically acceptable salt thereof to a patient having such an allergy.

Suitable pharmaceutically acceptable salts include, for example, ammonium salts, alkali metal salts (e.g. sodium, potassium and lithium), alkaline earth metal salts (e.g. magnesium and calcium), and salts with organic amines (e.g. mono- di- or trialkyl C 1 to 6 amines, piperidine, and trialkanol C 1 to 6 amine salts).

The active ingredient may be administered as a pharmaceutical composition which may contain a pharmaceutically acceptable excipient, diluent or carrier.

Examples of suitable adjuvants are:

For tablets and dragées: Binders, for example, cellulosic materials, e.g. microcystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic diluents, e.g. talc.

For syrups, suspensions or dispersions; A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilisers and dispersing agents.

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the active ingredient particles themselves or granules thereof made with for example sucrose and of a size up to 2 mm in diameter with a layer of, e.g. beeswax, Carnuba wax, stearic or palmitic acids, cetyl alcohol or similar substances which could be expected to be slowly dissolved or digested or to act as a semi-permeable membrane through which the active ingredient can diffuse when the preparations are ingested. The compositions may contain active ingredient particles or granules which are uncoated in admixture with particles or granules having one or more coats of the coating medium, and may be in the form of a capsule containing the particles or granules or alternatively a tablet, for which other adjuvants may be required, such as glidants or lubricants. The active ingredient may be administered as an enteric coated composition to make it available at the appropriate part of the gastro-intestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The active ingredient may, if desired, be used in a specific form, e.g. having a substantial number of particles of effective particle size of less than 10 microns or particular crystal habit.

The active ingredient may also be formulated as an aqueous, e.g. a water:chloroform (400:1), solution containing from 0.001 to 10.0% by weight thereof. The active ingredient in free acid form may conveniently be administered as an aqueous suspension containing from 0.1 to 10%, e.g. about 2% by weight thereof.

The dosage to be administered will of course vary with the patient, the condition to be treated, with its severity and with its location. However, in general a dosage of from about 20 to 1,000 preferably 100 to 750 and more preferably 200 to 500 mg of the active ingredient administered 1 to 4 times a day (i.e. a daily dosage of 20 to 4,000 mg) is found to be satisfactory. We also provide a method in which the dosage is from 20 to 250 mg of the drug administered 2 to 4 times a day, i.e. a daily dosage of from 40 to 1,000 mg of active ingredient. The administration preferably takes place before, e.g. about 30 minutes before, the patient takes food.

Conditions which may be treated by the present method include hypogammaglobulinemia, allergies to ingested milk, egg, fruit, fish, nuts, shellfish, meat, vegetables and creal flour (gluten).

Especially preferred is the disodium salt of 1,3-bis(2-carboxychromon-5-yloxy)-2-hydroxypropane.

The invention is illustrated, but in no way limited by the following Examples.

EXAMPLE 1

Four infants who were not tolerant to milk protein were given a solution of the di-sodium salt of 1,3-bis(2-carboxychromon-5-yloxy)-2-hydroxypropane (5 mls, 50 mg of the di-sodium salt) orally every 6 hours during their waking hours for a period of 7 days.

All four infants tolerated milk protein from the second to the seventh day of the treatment.

EXAMPLE 2

A 33-year old female was allergic to fruit and fish, developing an urticiarial rash of face, arms and blush areas 10 to 12 hours after eating fruit, which lasted 24 to 48 hours, and vomiting after eating fish. 30 Minutes prior to challenge with 4 oz fried cod, 100 mg of the disodium salt of 1,3-bis(2-carboxychromon-5-yloxy)-2-hydroxypropane (sodium cromoglycate) was administered orally in the form of a powder contained in a gelatine capsule. The vomiting reaction was blocked. Similar treatment with 200 mg of sodium cromoglycate 30 minutes prior to ingestion of 4 oz strawberries blocked the urticarial reaction.

EXAMPLE 3

Sixteen children (mean age 6.5 years, range 1.7–16 years) all had a long history of food allergy, giving rise to chronic allergic symptoms including rhinitis, gastrointestinal symptons and urticaria. A wide variety of foods caused the symptons. Twelve were allergic to eggs and fruit or nuts, eight to fish or meat and five to vegetables. Six of the children were allergic to one food only, and nine were allergic to at least 8 foods. The patients were assessed in a double blind crossover trial where either 400 mg of disodium cromoglycate or a placebo was administered. In 10 cases the disodium cromoglycate was the more effective treatment, and in 4 there was no difference.

EXAMPLE 4

13 Children ranging from 12 months to 5 years of age (9 males and 5 females) all affected by very severe eczema in the chronic phase and some also affected by atopic symptoms, were selected.

Apart from eczema one girl had a history of collapse after milk intake, and another patient had a history of chronic diarrhea.

The patients, after clinical examination and growth evaluation, were submitted to Mc Ewan's elimination diet for two weeks after which they were challenged in order to identify the specific food allergens.

The challenges showed that the most important allergens were: eggs (11/13 i.e. 84,6%), milk (11/13 i.e. 84,6%) and fish (2/13 i.e. 15%).

Challenges resulted positive for only one allergen in four children, for two allergens in seven children and for three allergens in the remaining two children.

Subsequently, the patients were put on a free diet and when skin symptoms were showing again, disodium cromoglycate was introduced at a dosage of 200 mg four times per day (diluted in 30 ml of water) for 45 days, administered 15 minutes before meals. This dosage was doubled in case of absence of activity. Patients were instructed to complete a diary card for a number of symptoms such as itch, eczema, urticaria, bowel discharge frequency and the other clinical manifestations of allergy. Clinical evaluation of the efficacy, and growth evaluation were carried out at the end of the treatment period.

One patient was excluded from the final evaluation because he had not followed the therapy correctly. Two patients were also excluded because their parents refused to have blood samples taken at the end of the treatment.

Results

The elimination diet caused complete remission of symptomatology in 12 patients and fair attenuation in 1.

The treatment with the disodium cromoglycate was effective in 8 cases out of 12 at daily dosage of 800 mg.

In the remaining 4 cases, posology was doubled. The increase in posology gave good results in two cases and drastically reduced itch, but not skin symptoms, in another case.

Nine out of 12 subjects (75%) showed by the end of the treatment an increase in body weight (calculated by Tanners' tables) which was particularly evident in those children who before the trial had a body weight less or equal to the third percentile.

No significant side effects were reported.

After the end of the trial the children continued the free diet and symptoms reappeared in all but one in a lapse of time ranging from 2 weeks to 2 months.

EXAMPLE 5

Twenty children, ranging in age from 1 to 15 years, with a diagnosis of food allergy were selected. Most children had a long history of allergic illness with eczema as one of the dominating symptoms. The children were allergic to a wide variety of foods of which the most common were egg, fish, fruit/nut, vegetables, milk, chocolate, dyes and penicillin. On challenge with these foods the most common manifestations were eruption of eczema, urticaria, circumoral rash and itching (ten patients), but also gastrointestinal symptoms were common (eight patients). Only two patients were free from symptoms on elimination diet during the trial.

Four patients did not conform to protocol and were excluded from the analysis.

The trial was carried out on a double-blind cross-over basis in which the active treatment was sodium cromoglycate and the placebo was glucose, both given orally, dissolved in 10 ml of water, at a dose of 100 mg four times a day 30–60 min before meals. Each patient entering the trial was allocated at random to a drug sequence (drug-placebo or placebo-drug) and received treatment with drug and placebo, each for a period of 3 weeks. For the third week of the two treatment periods, the parents were instructed to give the child a food to which the child was allergic in quantities usually sufficient to give symptoms. The clinician was continuously informed and decided if the food should be given again the following day or if the amount was to be increased. Thus, the number of days during which the children were challenged varied from 1 to 7 days. Following the first treatment period there was a 2-week wash-out period during which the child reverted to the ordinary elimination diet and then commenced a second 3-week treatment period with the alternative treatment. Diary cards were completed by the parents with daily recordings on a four point scale (0–3) of the severity of three different kinds of symptoms from the skin, respiratory and gastrointestinal tract. On the basis of symptoms reported daily after each challenge the response to the food challenge was recorded by the clinician on a four point scale (0–3). At the end of the trial, preferences by both the clinician and the parents were recorded. The patients were examined five times during the trial.

At the end of the trial both the clinician and the parents were asked to state a preference for either treatment period. For parents' preferences, eleven were in favour of the drug period ($P<0.05$). Similarly the clinician's preference was significantly ($P<0.05$) in favour of the drug period.

In five children a remarkable relief of skin sumptoms was seen during drug treatment. On challenge a lower mean challenge score was achieved during drug treatment compared to placebo ($P=0.05$). The mean symptom score for the week during which allergen was taken was lower for the drug period.

EXAMPLE 6

The patients were selected on the basis of positive clinical histories, positive provocation on repeated challenges, positive prick test and positive radioallergosorbent tests. Sixteen patients, 14 females and two males, whose mean age was 32 years (range 5–67 years) took part in this study. The clinical manifestations of these patients included urticaria, abdominal pain, purpura, swelling and itching of eyes, sneezing, rhinitis angiodema, itching, abdominal distension, pruritis, headache, geographic tongue and itching in the mouth.

In the pre-trial phase the amount of the suspected food and the allergic responses were determined. The patient was then started on 50 mg of disodium cromoglycate (or a matching placebo dextrose) four times a day, one capsule to be swallowed an hour before each meal and one at bed time. A diary card was supplied to the patient to record daily symptoms and medications taken. One the fifth day, one hour after the first dose of disodium cromoglycate, the patient was challenged with the offending food and the immediate allergic reactions noted. The delayed reactions were also noted on the diary card by the patient. In the second week cross-over between the drug and the placebo takes place, with similar challenges on day five. Using this double-blind method, about half of the total numbers of patients were on the active drug in the first week of the trial and the other half were on the placebo. At each visit (fifth and the seventh day during the trial period) of the patient, height, weight, blood pressure, pulse and respiratory rates were noted. The diary cards were checked for completeness and accuracy. The clinical condition was evaluated and a physical examination done.

After the second week, if the allergic reactions occur after both challenges, the patients entered Phase C in which the dose of the drug (or placebo) was 100 mg qid. However, if no reaction occurred after both challenges, the dose was reduced to 25 mg four times a day (Phase D). In come of the patients the dosage had to be increased to 150 mg qid.

One patient absconded. One 17-year old girl discontinued after two days because of abdominal pain, headache and nausea. When the code was broken she was on placebo. Four patients did not improve. Of the 16 patients, 10 (62.5%) had remission of symptoms of food allergy while taking the active drug.

EXAMPLE 7

Fourteen patients were included in the study (three males and 11 females; age ranging from 8 to 63) all of them having a history of symptoms of allergic type, appearing within 24 h after ingesting a known quantity of food. A controlled challenge test carried out with the food gave a positive result. Symptoms disappeared in all of them within 48 h or shortly thereafter.

The study was conducted in three parts.

In Part 1, a dose of 200 mg or more of disodium cromoglycate was administered orally 30 min before a challenge with the selected food. The dose of drug was increased or decreased in a second or third challenge in order to establish the minimum effective dose.

In Part 2, each patient was challenged on five separate occasions (once or twice a week, and always when symptoms from a previous challenge had subsided completely). Drug (based upon the dose chosen in Part 1) or placebo, was orally administered prior to each food challenge, according to a double-blind, randomized schedule. Results were considered positive when clinical symptoms appeared after the ingestion of the food, that is to say, when drug or placebo did not succeed in preventing symptoms from occurring, and negative when symptoms did not occur.

In Part 3, the individual dose of drug chosen in Part 1 was administered three or four times daily for 4 weeks, 20 min before meals, on a full diet, including the previously non-tolerated foods. The patients were clinically controlled each week and full haematology and biochemistry were monitored.

In Part 1 of the study protection against challenge was achieved in all cases by means of a dose of from 100 to 800 mg of disodium cromoglycate.

When the code was broken, for Part 2, it was found that drug had been administered on three occasions when a positive reaction occurred, and on 27 when the result of challenge tests was negative. Placebo had been administered 32 times, 22 of them followed by a positive challenge result and 10 without clinical reaction. The percentage positive responses to challenge for both active and placebo preparations have been compared using a Wilcoxon Matched Pairs Signed Ranks Test. The results of this analysis show a positive benefit in favour of disodium cromoglycate which is significant at a rate of $P<0.01$.

In Part 3 of the study a good tolerance to a full diet, including the previously non-tolerated foods, was achieved in nine patients, and an incomplete tolerance in one. According to the results obtained in this double-blind randomized study, disodium cromoglycate proved to be undoubtedly effective in preventing symptoms of food allergy from occurring not only in the gastrointestinal tract but also in other target organs (as with e.g. urticaria).

EXAMPLE 8

Patients selected for study were first challenged with increasing amounts of the food to which they were sensitive, in order to determine the amount of the food required consistently to produce symptoms. They were then asked to take disodium cromoglycate 50 mg, dissolved in approximately 50 ml of warm water, to swil it round the mouth and then to swallow it half an hour before the three main meals of the day and at bedtime for three days. On the second day of the trial the food to which the patients had reacted adversely was given instead of breakfast. If symptoms were not prevented the study was repeated with the dose of drug increased to 100 mg. If symptoms were prevented by either 50 or 100 mg, taken four times daily, the subject was admitted to the double-blind trial. The placebo was dextrose; in the amount given its taste was indistinguishable from drug. 20 Subjects, aged 3 to 61, entered and completed the double-blind trial. 14 were benefited by the drug, 1 by placebo, 3 by neither. 2 had no untoward reactions to cow's mild (the food to which they had appeared initially to be sensitive) on either drug or placebo. The results indicate that a significant degree of protection was provided by oral disodium cromoglycate ($P<0.001$).

I claim:

1. A method of treatment of an allergy to an ingested allergen, which comprises per os administration of a daily dosage of from 20 to 4,000 mg of 1,3-bis(2-carboxychromon-5-yloxy)-2-hydroxypropane or a therapeutically acceptable salt therof, as active ingredient to a patient having such an allergy.

2. The method of claim 1, wherein the salt is an ammonium, alkali metal or alkaline earth metal salt.

3. The method of claim 1, wherein the compound is the disodium salt of 1,3-bis(2-carboxychromon-5-yloxy)-2-hydropropane.

4. The method of claim 1, wherein the patient receives unit doses of from 20 to 1,000 mg of the active ingredient.

5. The method of claim 4, wherein the unit doses are from 100 to 750 mg of active ingredient.

6. The method of claim 5, wherein the unit doses are from 200 to 500 mg of active ingredient.

7. The method of claim 1, wherein the patient receives from 40 to 1,000 mg of active ingredient per day.

8. The method of claim 1, wherein the allergy treated is an allergy to ingested milk, eggs, fruit, fish, nuts, shellfish, meat, vegetables or cereal flour.

* * * * *